US 9,810,543 B2

(12) United States Patent
Hoch et al.

(10) Patent No.: US 9,810,543 B2
(45) Date of Patent: Nov. 7, 2017

(54) METHOD AND DEVICE FOR CARRYING OUT TRAVEL ROUTE PLANNING FOR A VEHICLE

(71) Applicant: Volkswagen Aktiengesellschaft, Wolfsburg (DE)

(72) Inventors: Nicklas Hoch, Hannover (DE); Bernd Werther, Braunschweig (DE)

(73) Assignee: Volkswagen Aktiegesellschaft, Wolfsburg (DE)

( * ) Notice: Subject to any disclaimer, the term of this patent is extended or adjusted under 35 U.S.C. 154(b) by 0 days.

(21) Appl. No.: 14/043,348

(22) Filed: Oct. 1, 2013

(65) Prior Publication Data

US 2014/0052374 A1   Feb. 20, 2014

Related U.S. Application Data

(63) Continuation of application No. PCT/EP2012/001127, filed on Mar. 14, 2012.

(30) Foreign Application Priority Data

Apr. 1, 2011   (DE) .................. 10 2011 015 775

(51) Int. Cl.
  *G01C 21/34*   (2006.01)
  *G01C 21/36*   (2006.01)
  (Continued)

(52) U.S. Cl.
  CPC ............ *G01C 21/3469* (2013.01); *A61B 5/18* (2013.01); *G01C 21/343* (2013.01);
  (Continued)

(58) Field of Classification Search
  CPC ....... G08G 1/14; G01C 21/26; G01C 21/3685
  See application file for complete search history.

(56) References Cited

U.S. PATENT DOCUMENTS 5,272,638 A   12/1993   Martin et al.
5,790,976 A *   8/1998   Boll et al. .................. 455/456.5
          (Continued)

FOREIGN PATENT DOCUMENTS

CN   1811803 A   8/2006
CN   101236095 A   8/2008
          (Continued)

OTHER PUBLICATIONS

International Search Report dated Jul. 31, 2012.
Chinese Office Action for Chinese Application No. 201280016193.9 dated Jun. 9, 2015 with English translation.

*Primary Examiner* — Rami Khatib
*Assistant Examiner* — Nicholas K Wiltey
(74) *Attorney, Agent, or Firm* — Muncy, Geissler, Olds & Lowe, P.C.

(57) ABSTRACT

A method and device for carrying out travel route planning for a vehicle, in which schedule data are transmitted to a calculation unit, which is coupled to a data memory, in which data relating to a path network for the vehicle and data relating to the geographic positions of energy supply facilities are stored. The calculation unit checks if a route sequence which connects the geographic positions of the destinations associated with the schedule data is calculable such that the destinations are reached at the associated time data of the schedule data, wherein the prognosticated residual energy amount in the energy store of the vehicle for travelling the route sequence is determined and taken into account, if no such route sequence is calculable using the calculation unit, the latter determines matched schedule data for which such a route sequence is calculable, and the matched schedule data are output.

15 Claims, 8 Drawing Sheets

H Home P Appointment + Parking lot [. .] Charge process + Charging station

(51) Int. Cl.

| | | |
|---|---|---|
| *G06Q 10/10* | (2012.01) | |
| *A61B 5/18* | (2006.01) | |
| *A61B 5/0205* | (2006.01) | |
| *A61B 5/021* | (2006.01) | |
| *A61B 5/024* | (2006.01) | |
| *A61B 5/0402* | (2006.01) | |
| *A61B 5/08* | (2006.01) | |
| *A61B 5/145* | (2006.01) | |

(52) U.S. Cl.
CPC ......... *G01C 21/362* (2013.01); *G06Q 10/109* (2013.01); *A61B 5/021* (2013.01); *A61B 5/024* (2013.01); *A61B 5/0205* (2013.01); *A61B 5/0402* (2013.01); *A61B 5/0816* (2013.01); *A61B 5/14542* (2013.01)

(56) References Cited

U.S. PATENT DOCUMENTS

| | | | |
|---|---|---|---|
| 5,815,824 A | 9/1998 | Saga et al. | |
| 7,444,237 B2 | 10/2008 | Dale | |
| 7,516,010 B1 * | 4/2009 | Kaplan | G01C 21/30 340/932.2 |
| 8,606,517 B1 * | 12/2013 | Ehrlacher et al. | 701/465 |
| 2002/0055818 A1 * | 5/2002 | Gaspard, II | 701/209 |
| 2002/0161520 A1 * | 10/2002 | Dutta et al. | 701/213 |
| 2003/0055554 A1 | 3/2003 | Shioda et al. | |
| 2010/0106401 A1 * | 4/2010 | Naito et al. | 701/201 |
| 2010/0228574 A1 * | 9/2010 | Mundinger et al. | 705/4 |
| 2010/0280853 A1 * | 11/2010 | Petralia et al. | 705/5 |
| 2011/0032110 A1 | 2/2011 | Taguchi | |
| 2011/0074350 A1 * | 3/2011 | Kocher | B60L 11/1816 320/109 |
| 2011/0130885 A1 * | 6/2011 | Bowen | B60L 3/12 700/291 |
| 2011/0191126 A1 * | 8/2011 | Hampshire et al. | 705/5 |
| 2011/0238289 A1 * | 9/2011 | Lehmann et al. | 701/201 |
| 2011/0288765 A1 * | 11/2011 | Conway | G01C 21/3469 701/533 |
| 2011/0313648 A1 * | 12/2011 | Newson et al. | 701/200 |
| 2012/0161984 A1 * | 6/2012 | Amir | 340/932.2 |
| 2012/0179420 A1 * | 7/2012 | Gilman | B60K 35/00 702/165 |

FOREIGN PATENT DOCUMENTS

| | | |
|---|---|---|
| CN | 101344399 A | 1/2009 |
| DE | 195 19 107 C1 | 4/1996 |
| DE | 10 59 746 A1 | 10/2001 |
| DE | 101 46 789 A1 | 4/2003 |
| DE | 103 02 504 A1 | 9/2004 |
| DE | 10 2004 022 265 A1 | 12/2005 |
| DE | 10 2005 055 243 A1 | 5/2007 |
| DE | 10 2008 030 563 A1 | 12/2009 |
| DE | 10 2009 053 982 A1 | 6/2010 |
| DE | 10 2010 039 075 A1 | 2/2011 |
| EP | 1 201 849 A2 | 5/2002 |
| EP | 1 300 817 B1 | 4/2006 |
| EP | 1 909 069 A1 | 4/2008 |
| EP | 1 944 724 A1 | 7/2008 |
| EP | 1 975 561 A2 | 10/2008 |
| JP | 2008-096144 A | 1/2009 |
| JP | WO2011001595 A1 * | 1/2011 |

* cited by examiner

H Home  P Appointment + Parking lot  [. .] Charge process  + Charging station

H Home  P Appointment + Parking lot  [. .] Charge process  + Charging station

H Home P Appointment + Parking lot [. .] Charge process + Charging station

H Home P Appointment + Parking lot [. .] Charge process + Charging station

H Home P Appointment + Parking lot [. .] Charge process + Charging station

H Home P Appointment + Parking lot [. .] Charge process + Charging station

H Home P Appointment + Parking lot [. .] Charge process + Charging station

H Home P Appointment + Parking lot [. .] Charge process + Charging station

METHOD AND DEVICE FOR CARRYING OUT TRAVEL ROUTE PLANNING FOR A VEHICLE

This nonprovisional application is a continuation of International Application No. PCT/EP2012/001127, which was filed on Mar. 14, 2012, and which claims priority to German Patent Application No. DE 10 2011 015 775.1, which was filed in Germany on Apr. 1, 2011, and which are both herein incorporated by reference.

BACKGROUND OF THE INVENTION

Field of the Invention

The present invention relates to a method and a device for carrying out travel route planning for a vehicle.

Description of the Background Art

A vehicle user often faces the problem that he must keep various appointments at different locations within a specific time period. For this purpose, travel route planning for the vehicle should be carried out. The travel route should be planned so that the user reaches the locations where the appointments take place in a timely fashion with the vehicle. It must be considered in this regard that from time to time the energy storage device needs to be replenished. Particularly in the case of electric vehicles it is necessary to include the recharging of the battery as conveniently as possible in the travel route planning, because the range of an electric vehicle is usually much shorter than the range of a conventional vehicle, which is powered by means of a fuel.

DE 195 19 107 C1, which corresponds to U.S. Pat. No. 5,790,976, and which discloses a travel route guidance device particularly for an electric vehicle. The described device comprises a data input unit for entering one or more destinations for a trip and a road network memory for storing the locations on the road network travelable by the vehicle and the associated distances to locations. Further, the device comprises a computing unit for determining one or more possible trip routes from the vehicle location to the destinations including the necessary energy supplying processes at one or more energy supply locations depending on the amount of energy present in the energy storage device, the energy supply network, and the route-specific energy consumption. Finally, the device comprises a display unit for displaying the routes determined by the computing unit.

DE 10 2004 022 265 A1 discloses a method for drawing up a route from a starting point to a destination in a navigation system. In the method, a factor that influences the energy consumption for traversing the route is taken into account in drawing up the route.

DE 100 59 746 A1 discloses a method for computer-aided travel route planning and travel route guidance, which takes into account dynamic changes in the traffic situation and changes in appointments.

A navigation data providing system is known from EP 1 300 817 B1, which corresponds to US 2003/0055554. In this system, drive plan data are sent out which are selected as a function of user preference data. The drive plan data are received by a navigation terminal and used for route guidance for the vehicle.

EP 1 201 849 A2, describes a method and device for allocating parking spaces. In the method, an enquiry is made over a radio unit in a vehicle about a possibility of parking to the device for allocating parking spaces. This enquiry contains information on the current position of the vehicle. The device determines the next free parking option from this and transmits this as destination information to the vehicle. Next, the expected arrival time is calculated and the availability of the determined parking option is checked at a predetermined lead time before the expected arrival time. If the parking option is free, it is possible to reserve it for the vehicle. If the parking option is no longer free, the device determines a new parking option and transmits the corresponding information to the vehicle.

DE 103 02 504 A1 discloses a method for determining the range of an electric vehicle. In the method, vehicle, route, and/or environmental information for the vehicle and a planned or a currently driven route are acquired and processed by a vehicle computer. The remaining range of the electric vehicle is calculated from this information and displayed.

DE 10 2005 055 243 A1 discloses a method for determining an energetically favorable travel route for a vehicle. In the method, the starting point and endpoint of the route are entered. Further, vehicle-related information, particularly load information, is provided. The provided vehicle-related information is compared with stored route data in the form of vehicle-related information and energy consumption. Thereupon, a driving route with minimized energy consumption based on the stored route data is selected depending on the provided vehicle-related information and the starting point and endpoint. Finally, the data on the selected route are output.

DE 10 2009 053 982 A1 discloses a system for calculating a consumption-optimized route for a motor vehicle. The system has a position receiver, a traffic information receiver, and a computing unit with whose aid a route to a destination is calculable. The computing unit can calculate a consumption-optimized route by using vehicle-individual and/or driver-individual consumption-relevant data.

SUMMARY OF THE INVENTION

It is therefore an object of the present invention to provide a method and a device, with which optimal travel route planning can be carried out as a function of schedule data. The method and device can be applied to a vehicle, whereby the vehicle can include an energy storage device for storing the energy to power the vehicle, particularly a rechargeable battery. In addition or alternatively, powered via fuel can also be provided. The vehicle can be a so-called electric vehicle or a so-called hybrid vehicle The vehicle, for which the travel route planning is to be carried out, comprises an energy storage device for storing energy for driving the vehicle, for example, a rechargeable battery and/or a fuel tank. The invention relates in particular to day trip planning within the area of mobility with electrically powered vehicles or vehicles for which the spatial density of energy supply facilities is low, as is currently the case, e.g., for gas-powered vehicles or vehicles with a fuel cell drive system. In this case, in particular the time required to replenish the energy storage device of the vehicle is also taken into account.

According to a first aspect of the invention, in the method of the invention a destination sequence for the travel route to be planned is transmitted to a computing unit. The computing unit is coupled to a data memory, in which data on a road network and data on the geographic positions of parking areas comprising parking lots or energy supply facilities are stored for the vehicle. The computing unit calculates a route sequence. In this regard, a predicted remaining amount of energy in the energy storage device is calculated for traveling the route sequence. Further, in each case parking areas, assigned to the destinations, near the particular destination are determined for the destinations of the destination sequence. For each destination of the destination sequence, an assigned parking area is determined, whereby in the determination of the distance of the parking area from the assigned destination, the geographic position of the next destination, or the geographic positions of the parking areas of the next destination, and/or the predicted remaining amount of energy in the energy storage device for traveling the route sequence are considered. The route sequence then comprises routes between parking areas of successive destinations of the destination sequence. Finally, the calculated route sequence can be output or transmitted in the method.

A destination sequence can be understood to be a series of geographic positions, which are connected one after the other by the travel route to be planned. Accordingly, a route sequence is understood to be a series of routes that connects the destinations or the parking areas assigned to the destinations.

In the method of the invention according to the first aspect of the invention, in the determination of parking areas assigned to a destination, the destination can be expanded to a destination area. The destination area can contain the destination and the assigned parking areas. The size of said destination area can depend, for example, on the maximum distance that a parking area may be located from the destination. If the destination area has been defined, the parking areas are determined whose geographic positions fall within the destination area. In the selection of the parking area, in the method of the invention, not only the distance of the parking area from the assigned destination is considered but also the next destination, as well as optionally the previous destination in the route sequence and the predicted remaining amount of energy in the energy storage device. In the method of the invention, according to the first aspect, the travel route planning is thus carried out advantageously with consideration of different possible parking areas for the vehicle when a destination of the destination sequence is reached. In this way, the route between the destinations of the destination sequence can be optimized. Further, replenishing of the energy storage device can be taken into account, because a selected parking area can also comprise an energy supply facility. Therefore, optimized travel route planning can be carried out for the predetermined destination sequence.

According to an embodiment of the method of the invention, the computing unit automatically decides, depending on the predicted remaining amount of energy in the energy storage device for traveling the route sequence, whether a parking lot or an energy supply facility is selected as the parking area. It can therefore be assured advantageously by selection of the parking area that while traveling the route sequence the vehicle has sufficient energy reserves at all times for driving the vehicle and possibly for the internal consumers of the vehicle. This is particularly important when the vehicle is an electric vehicle with a relatively short range.

According to an embodiment of the method of the invention, the computing unit decides further automatically which parking areas are selected depending on the energy cost for filling the energy storage device of the vehicle.

According to an embodiment of the method of the invention, schedule data, comprising the geographic positions of at least one part of the destinations of the travel route to be planned and the associated time data, can be transmitted to the computing unit. In this case, in determining the parking areas the computing unit takes into account the predicted remaining amount of energy in the energy storage device for traveling the route sequence, the time data for the destination assigned to the parking area, and the length of time for increasing the energy reserves in the energy storage device by means of the energy supply facility.

The computing unit thus can determine from the schedule data the location information for the destination sequence and the times when the vehicle must reach the destinations. Further, the computing unit can determine how long the vehicle remains at a destination from the schedule data. The travel route can be planned particularly so that a parking area is selected, which comprises an energy supply facility, whereby the energy storage device is filled while the vehicle remains at a destination. In order to optimize the travel route, it can be taken into account in the method that it is not absolutely necessary that the energy storage device is filled to a maximum at an energy supply facility. When the end of a schedule is reached, the filling of the energy storage device can be cut short, if appropriate, before the energy storage device is filled to the maximum. As a result, unnecessary waiting periods for the user are advantageously avoided, which are caused by the filling of the energy storage device. The time during which the vehicle is not in use during a user's appointment can be used optimally for filling the energy storage device, without additional waiting times resulting for the user.

According to an embodiment of the method of the invention, the computing unit determines for the parking areas in addition the distance from the assigned destination or the time a user needs for going from the parking area to the assigned destination. The computing unit in this case during the determination of the parking areas can take into account further the determined duration or the distance and the schedule data. In this regard, it can also be considered whether the user will go by foot from the parking area to the destination or reaches the destination in some other way. Further, a user-dependent walking speed can be taken into account.

In the method, particularly the route sequence is optimized by the computing unit with respect to the energy consumption in traveling the route sequence and/or with respect to the time for traveling the route sequence. It is assured further that the destinations of the destination sequence are reached in keeping with the schedule data, whereby not only the time for reaching the parking area, assigned to a destination, is taken into account but also the subsequent time for reaching the destination.

According to an embodiment of the method of the invention, the computing unit determines furthermore the probability of parking area availability. The availability probability is taken into account in determining the parking areas. If it is relatively unlikely that a parking space is free at the required time, which results from the route sequence, a different parking area can be selected. In this respect, the availability probability of the parking area is set in relation to the worsening of the route sequence by the other parking area. The travel route planning can be advantageously optimized further in this way. The probability of parking area availability is determined in particular based on the arrival time of the vehicle at the parking area and the duration of stay at the parking area. Further, the computing unit can fall back on historical data, for example, which indicate statistically the times at which the individual parking areas were occupied or free in the past. In addition, already made reservations by third parties for the parking spaces can be taken into account in the availability probability.

Furthermore, the driving behavior of a specific user can be predicted in the route sequence calculation. For example, it can be determined from the historical data for a specific driver how rapidly or slowly he drives. Profiles for specific drivers can be derived from this.

According to an embodiment of the method of the invention, the computing unit calculates the predicted remaining amount of energy in the energy storage device based on the predicted energy consumption during traveling of the route sequence. In this case, on the one hand, the predicted energy consumption for driving the vehicle and, on the other, the predicted energy consumption of the internal consumers of the vehicle are taken into account. This predicted energy consumption is then taken into account in the predicted remaining amount of energy in the energy storage device during the traveling of the route sequence. It is advantageously taken into account in the case of an electric vehicle that the energy consumption also depends on the battery charge state. If the battery charge state is rather low, a greater change in the charge state when traveling a route results than when the battery charge state is higher. If the vehicle is powered by a fuel, it is considered in this case that the fuel consumption due to the change in the weight of the vehicle also depends on the remaining amount of fuel in the vehicle.

In the prediction of energy consumption by internal consumers of the vehicle, weather forecasts or the season in which the route sequence is to be traveled can be taken into account. If it turns out that the ambient temperature is presumably very high when traveling the route sequence, it can be considered in predicting the energy consumption due to internal consumers that the air conditioning system of the vehicle will be turned on with a high probability when traveling the route sequence. In addition, features of the road network of the route sequence, particularly road grades and delays or accelerations because of curves can be taken into account. These features of the road network affect the energy consumption in traveling the route sequence.

According to an embodiment of the method of the invention, user-specific constraints are transmitted to the computing unit. The computing unit takes these user-specific constraints into account in determining the parking areas. The user can indicate preferences as constraints. For example, the user can indicate the priority of assuring that a specific remaining amount of energy is always stored in the energy storage device. This constraint can give the user a sense of security of having sufficient energy in the energy storage device of the vehicle in the event of possible unforeseen changes in the schedule in order to be able to react to these changes. Further, the user can indicate the priority that appointments be kept on time. Alternatively, he can indicate specific acceptable time delays. In this case, it can also be considered in the travel route planning that the appointments in the route sequence cannot be kept precisely, but the optimal route sequence is much better than the next best route sequence, so that minor delays are tolerated within the scope of the user's specifications.

Furthermore, the user can indicate priorities with respect to parking areas. For example, he can set as a constraint the maximum distance between a parking area and the destination. Further, he can indicate a preference for a specific parking space type such as, for example, a handicapped parking space.

After a route sequence has been calculated by the method of the invention, the calculated route, sequence is output, for example, by means of a display in conjunction with a geographic map. Further, the parking areas associated with the route sequence can be automatically reserved by transmitting the relevant data to a corresponding device for reserving parking spaces. Furthermore, the calculated route sequence can be sent to a device in the vehicle.

According to an embodiment of the method of the invention, during the traveling of the calculated route sequence, the remaining amount of energy in the energy storage device of the vehicle is determined and compared with the predicted remaining amount of energy of the vehicle for a corresponding route position. If the deviation of the determined remaining amount of energy from the predicted remaining amount of energy exceeds a limit, the route sequence is recalculated based on the determined remaining amount of power. The method of the invention is thus used not only to carry out travel route planning before the start of the journey. Rather, it can also be checked during the trip whether the predictions made in calculating the route sequence were correct. In particular, the predictions on energy consumption of the vehicle when traveling the route, i.e., the predicted remaining amount of energy at the individual route positions, are compared with the actual remaining amount of power. The route sequence is recalculated if deviations exceed a specific limit value, which may also be 0. This calculation can be made according to the previously performed calculation. The limit value can be, e.g., a deviation of 5% or 10%.

It is possible to check, furthermore, whether due to the deviation of the actual remaining amount of energy from the predicted remaining amount of energy a specific destination of the destination sequence can no longer be reached, because the energy for driving the vehicle is no longer sufficient for this. In such a case, the route sequence can be changed particularly so that the geographic position of an energy supply facility is inserted in the route sequence as an intermediate destination. It is advantageously assured hereby that the destinations of the destination sequence can be reached in each case, even if they are reached at a later time, so that certain appointments perhaps cannot be kept on time.

Furthermore, deviations from the actual values while traveling the route sequence can also occur with respect to other assumptions, made in the projection of the route sequence. For example, it is possible to check whether certain positions of the route sequence can be reached on time in accordance with the prediction. In this regard, data can also be considered which were generated from another vehicle currently taking part in traffic (so-called XFCD—extended floating car data). Furthermore, data from a vehicle-to-vehicle or vehicle-to-X communication can be considered as well. In this case also, the route sequence can be recalculated in the case of possible deviations. In addition, current traffic data can be considered. If said traffic data deviate from the assumptions in the projection of the route sequence, and possibly certain destinations cannot be reached in a timely fashion or in terms of energy or time, an adjusted route sequence can be calculated.

Furthermore, the availability probabilities for parking areas can also be updated during the trip by data transmission per radio. The computing unit can especially take into account current data on the occupation of parking areas, including the estimated length of occupation, and also adjust the route sequence so that other parking areas are selected different from those in the route sequence calculated in advance.

Finally, the route can also be rescheduled continuously during the trip and independent of certain events.

According to the first aspect of the invention, further a device for travel route planning for a vehicle is provided.

The vehicle comprises an energy storage device for storing the energy for driving the vehicle. The device comprises a computing unit and a data memory which is coupled to the computing unit and in which data on a road network and data on geographic positions of parking areas, comprising parking lots or energy supply facilities, are stored for the vehicle. Furthermore, the device comprises an interface which is coupled to the computing unit and via which a destination sequence for the travel route to be planned can be sent to the computing unit. Optionally, an output unit can be provided which is coupled to the computing unit and by means of which a route sequence calculated by the computing unit can be output, especially displayed. Alternatively or in addition, an interface for transmitting data on the calculated route sequence can also be provided. A route sequence can be calculated by the computing unit in the device of the invention, whereby the predicted remaining amount of energy in the energy storage device is calculated for traveling the route sequence. Parking areas, assigned to the destinations, near the particular destination are determined for the destinations of the destination sequence. An assigned parking area is determined for each destination of the destination sequence, whereby in the determination the distance of the parking area from the assigned destination, the geographic position of the next destination, or the geographic positions of the parking areas of the next destination, and/or the predicted amount of energy in the energy storage device for traveling the route sequence are considered. The route sequence then comprises routes between parking areas of successive destinations of the destination sequence.

The device of the invention is particularly suitable for carrying out the method of the invention described above. It therefore also has the same advantages as the method of the invention.

According to an embodiment of the device of the invention, it comprises an off-board module and an on-board module, whereby the off-board module comprises the computing unit. The off-board and on-board modules are coupled to one another via an interface at least at times in terms of data links, so that at least the route sequence can be transmitted from the off-board module to the on-board module. The on-board module comprises an additional computing unit, an additional output unit, a memory for storing a route sequence transmitted by the off-board module, and a sensor for determining the remaining amount of energy in the energy storage device of the vehicle. During the traveling of the calculated route sequence, the determined remaining amount of energy in the energy storage device of the vehicle can be compared by the additional computing unit with the predicted remaining amount of energy of the vehicle for a corresponding route position of the route sequence stored in the memory. If the deviation of the determined remaining amount of energy from the predicted amount of energy exceeds a limit value, the route sequence can be recalculated based on the determined remaining amount of energy and output via the output unit. It is thus advantageously possible to adjust the route sequence calculated in advance during the trip, when the actual remaining amount of energy in the energy storage device of the vehicle deviates from the predicted remaining amount of energy of the vehicle. Furthermore, in the case of deviations of other parameters, which were used during the precalculation of the route sequence, adjustments of the route sequence are made by the additional computing unit in the vehicle, as was explained above in reference to the method of the invention.

The travel route planning, i.e., particularly the calculation, planning, and optimization of the travel route, can occur by an off-board device, an on-board device, or divided between an off-board and an on-board device.

According to a second aspect of the invention, a method for performing a travel route planning for a vehicle is provided, in which schedule data, which comprise geographic positions of destinations of the travel route to be planned and associated time data, are transmitted to a computing unit, which is coupled to a data memory, in which data on a road network for the vehicle and data on the geographic positions of energy supply facilities are stored. In the method, the computing unit checks whether a route sequence is calculable, which connects the geographic positions of the destinations associated with the schedule data so that the destinations are reached at the associated time data of the schedule data, whereby the predicted remaining amount of energy in the energy storage device of the vehicle for traveling the route sequence is determined and taken into account. If the computing unit cannot calculate any such route sequence, the computing unit determines adjusted schedule data for which such a route sequence is calculable. The adjusted schedule data are then output.

In the method of the invention according to the second aspect, it is therefore not merely considered whether the energy reserves of the vehicle are sufficient to reach the destinations of the destination sequence. It is also being checked whether the appointments can be kept in terms of time with a calculated route sequence. If this is not the case, in the method of the invention according to the second aspect, a change in the schedule data is determined for which there is a route sequence which does not result in a conflict in the schedule data in terms of time. The predicted remaining amount of energy in the energy storage device of the vehicle is also considered at the same time, however; it is assured thereby that the destinations can be reached in terms of energy. It is also considered in the prediction of the remaining amount of energy that the amount of energy stored in the energy storage device of the vehicle can be increased at the geographic positions of the energy supply facilities, whereby in this case as well the energy storage device of the vehicle need not be completely filled at every energy supply facility.

In the check whether a route sequence is calculable that causes no conflict with the schedule data, the computing unit can test in particular different possible alternatives and check these for whether the geographic, time, and energy constraints are met.

In the check whether the destinations can be reached at the appropriate appointment starting times, a length of time to reach the destination is calculated during traveling of the route sequence. Numerous factors can enter into said calculation of the route duration. The route duration can depend, for example, on the time of day, weekday, possible holidays, and/or the expected traffic volume. Further, stored historical data can be used in order to be able to calculate more precisely the route duration for traveling at a specific time of day.

According to an embodiment of the method of the invention, in the adjusted schedule data geographic positions of destinations are assigned new time data. The route sequence thus continues to stop at each destination of the schedule data but at different times. As a result, a travel route planning can be advantageously provided in which the user can keep the intended appointments but nevertheless must postpone them. The user can simply find out by means of the travel route planning the times to which the appointments are to be postponed. After the appointments have been postponed, a route sequence is available that assures that the destinations can be reached in regard to time and energy.

If it is not possible to find a route sequence that also connects the destinations with changed time data by a route sequence, it is also proposed in the method of the invention that one destination or a number of destinations are deleted or postponed or the order of the destinations is changed. The adjustment of the user's appointments must also be made easier in this way for him, because it is calculated which destination must be eliminated or postponed, for example, in order to maintain a route sequence that connects the remaining destinations without a time or energy conflict. This change in the time data can also occur interactively with the user.

In the method of the invention, in calculating the route sequence, the computing unit optimizes in particular the time usable for the user of the vehicle. This usable time can be increased, for example, in that the amount of energy in the energy storage device of the vehicle is increased when the vehicle is not in use during a user's appointment. If necessary from the standpoint of energy, the computing unit selects for the route sequence the position of an energy supply facility near a destination, particularly at a parking area of the destination, so that the energy storage device of the vehicle can be recharged when the vehicle is not in use during an appointment.

According to the second aspect of the invention, a device for travel route planning for a vehicle is further proposed, said device comprising an energy storage device for storing the energy for driving the vehicle and having a computing unit and a data memory which is coupled to the computing unit and in which data on a road network and data on the geographic positions of energy supply facilities for the vehicle are stored. Furthermore, an interface coupled to the computing unit is provided, via which schedule data comprising geographic positions of destinations of the trip route to be planned and the associated time data can be sent to the computing unit. Further, the device comprises an output unit which is coupled to the computing unit and by means of which a route sequence calculated by the computing unit and/or adjusted schedule data can be output. The device of the invention according to the second aspect of the invention is characterized in that the computing unit can check whether a route sequence is calculable that connects the geographic positions of the destinations associated with the schedule data so that the destinations can be reached at the associated time data of the schedule data, whereby the predicted remaining amount of energy in the energy storage device of the vehicle for traveling the route sequence is determined and considered. If no such route sequence is calculable, schedule data adjusted by the computer can be determined for which such a route sequence is calculable.

The device of the invention according to the second aspect of the invention is especially suitable for carrying out the method of the invention according to the second aspect of the invention. Therefore, it also has the same advantages as the method according to the second aspect of the invention.

According to an embodiment of the device of the invention, the device can include an off-board module and an on-board module, whereby the off-board module comprises the computing unit. The off-board and on-board modules are coupled to one another via an interface at least at times in terms of data links, so that at least one route sequence can be transmitted from the off-board module to the on-board module. The on-board module comprises an additional computing unit, an additional output unit, a memory for storing a route sequence transmitted from the off-board module, and a sensor for determining the remaining amount of energy in the energy storage device of the vehicle. During the traveling of the calculated route sequence, the determined remaining amount of energy in the energy storage device of the vehicle can be compared by the additional computing unit with the predicted remaining amount of energy of the vehicle for a corresponding route position of the route sequence stored in the memory. If the deviation of the determined remaining amount of energy from the predicted remaining amount of energy exceeds a limit value, the additional computing unit can check whether the destinations of the route sequence continue to be reached at the associated time data of the schedule data, whereby the predicted remaining amount of energy in the energy storage device of the vehicle for traveling the route sequence is determined. If the check shows that the destinations of the route sequence cannot be reached at the associated time data, the additional computing unit calculates an adjusted route sequence or certain adjusted schedule data for outputting via the additional output unit.

The aforementioned features of the method of the invention and the device of the invention according to the first aspect of the invention can be combined individually or together with the method and the device according to the second aspect of the invention. Conversely, the individual features of the method and the device of the second aspect of the invention can also be combined individually or together with the method and device according to the first aspect of the invention.

According to a third aspect of the invention, a method is provided for carrying out a travel route planning for a vehicle, said method in which a destination sequence for the travel route to be planned is transmitted to a computing unit coupled to a data memory in which data on a road network for the vehicle are stored. The computing unit then calculates a route sequence that connects the destinations of the destination sequence. Further, a predicted remaining amount of energy in the energy storage device for traveling the route sequence is calculated. Furthermore, at least for the geographic position of the vehicle at a specific destination of the destination sequence, based on the predicted remaining amount of energy of the energy storage device of the vehicle and based on the stored road network, and a predicted energy consumption in traveling the road network the points of the road network are determined that can still be reached from a specific destination with the predicted remaining amount of energy at this specific destination. For at least the specific destination of the destination sequence, a graphic map display is generated in which the geographic position of this destination and the points of the road network are visualized that can still be reached from this destination with the predicted remaining amount of energy of the vehicle at this destination.

Therefore, a visualization of the remaining range for a route sequence calculated in advance is generated by the method of the invention according to the third aspect. An area reachable from this destination with the remaining amount of energy in the energy storage device of the vehicle is marked on a geographic map especially for each destination of the destination sequence. By means of this visualization the user is given an idea even during the planning of the route sequence, i.e., before the start of the trip, which regions he can still reach for each destination with the particular vehicle energy reserves. This display prevents in particular an uncertainty on the part of the user when using electric vehicles. In addition, by this visualization the user can still have an effect on the route planning easily and intuitively.

The visualization occurs, for example, in that an area of the graphic map display is marked off, whereby the marked-off area contains the reachable points of the road network. Further, the visualization can occur by means of a closed contour. According to a refinement of the method of the invention, further, data on geographic positions of energy supply facilities for the vehicle are stored in the data memory. In the geographic map display, the geographic positions of energy supply facilities are visualized that can still be reached from the specific destination with the predicted remaining amount of energy in the vehicle. Advantageously, the user can realize simply and intuitively in this way whether energy supply facilities can be reached when traveling a route sequence from a specific destination, so that the energy storage device of the vehicle can be replenished at any time.

According to an embodiment of the method of the invention, the route sequence contains as an intermediate destination or as a parking area the geographic position of an energy supply facility. For this intermediate destination, a graphic map display is generated in which the geographic position of this intermediate destination and the points of the road network are visualized that can still be reached before filling of the energy storage device at the energy supply facility and the points of the road network are also visualized that can be reached after the filling of the energy storage device at the energy supply facility. The user can so be informed of the remaining range before the filling of the energy storage device and after the filling of the energy storage device.

According to an embodiment of the method of the invention, a reference position is determined. It is assured in calculating the route sequence that the reference position is always within the remaining range of the vehicle. The reference position can be, for example, the user's place of residence or workplace. It can therefore be assured advantageously in calculating the route sequence that the user can return to this reference position at any time when traveling the route sequence. In this regard, the reference position is also within the remaining range of the vehicle when to reach the reference position the vehicle must drive to an energy supply facility for the vehicle as an intermediate destination. In this case as well, it is assured that the reference position can be reached in terms of energy.

According to an embodiment of the method of the invention, during traveling of the calculated route sequence the remaining amount of energy in the energy storage device of the vehicle is determined, and at least upon reaching a destination of the destination sequence an adjusted graphic map display is generated in which the geographic position of this destination and the points of the road network are visualized that can be reached from this destination with the determined remaining amount of energy in the energy storage device of the vehicle. The remaining amount of energy used as the basis in the precalculation of the route sequence is thereby checked based on the actual determined remaining amount of energy in the vehicle. In the case of possible deviations, an adjusted map display with visualization of the remaining range is displayed to the user, so that he can realize simply and intuitively whether the other destinations of the destination sequence are still within the remaining range. If this is not the case, the user or the computing unit can make automatic adjustments to the route sequence, as was already explained in reference to other aspects of the invention.

According to the third aspect the invention, a device for travel route planning for a vehicle is furthermore provided, said device comprising an energy storage device for storing the energy for powering the vehicle. The device has a computing unit and a data memory which is coupled to the computing unit and in which data on the road network for the vehicle are stored. Further, the device has an interface which is coupled to the computing unit and via which a destination sequence for the trip route to be planned can be transmitted to the computing unit. Further, an output unit is coupled to the computing unit. In the device of the invention according to the third aspect of the invention, a predicted remaining amount of energy in the energy storage device for traveling the route sequence is calculable by the computing unit. At least for the geographic position of the vehicle at a specific destination of the destination sequence, based on the predicted remaining amount of energy of the energy storage device in the vehicle and based on the stored road network and a predicted energy consumption during traveling the road network the points of the road network, can be determined that can still be reached from a specific destination with the predicted remaining amount of energy at this specific destination. For at least the specific destination of the destination sequence, a graphic map display can be generated and output by means of the output unit, in which the geographic position of this destination and the points of the road network are visualized that can still be reached from this destination with the predicted remaining amount of energy in the vehicle at this destination.

This device according to the third aspect the invention is designed particularly to carry out the method according to the third aspect of the invention. The device therefore also has the same advantages as the method according to the third aspect of the invention.

According to an embodiment of the device of the invention, the device has an off-board module and an on-board module, whereas the off-board module comprises the computing unit. The off-board and on-board modules are coupled to one another via an interface at least at times in terms of data links, so that at least the route sequence can be transmitted from the off-board module to the on-board module. The on-board module comprises an additional computing unit, an additional output unit, a memory for storing a route sequence transmitted by the on-board to the off-board module, and a sensor for determining the remaining amount of energy in the energy storage device of the vehicle. During the traveling of the calculated route sequence, the determined remaining amount of energy in the energy storage device of the vehicle can be compared by the additional computing unit with the predicted remaining amount of energy of the vehicle for a corresponding route sequence of the route sequence stored in the memory. If the deviation of the determined remaining amount of energy from the predicted remaining amount of energy exceeds the limit value, an adjusted graphic map display is generated in which the geographic position of a destination and the points of the road network are visualized that can be reached from this destination with the determined remaining amount of energy in the energy storage device of the vehicle. An adjustment of the visualization of the remaining range of the vehicle upon reaching a destination depending on the actual remaining amount of energy in the vehicle is achieved advantageously in this way.

The features of the method and device according to the third aspect of the invention can be used individually or in combination also in conjunction with the methods and the devices of the first two aspects of the invention. Conversely, the features of the methods and the devices of the first two aspects of the invention can be used individually or in combination with the method and the device according to the third aspect of the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
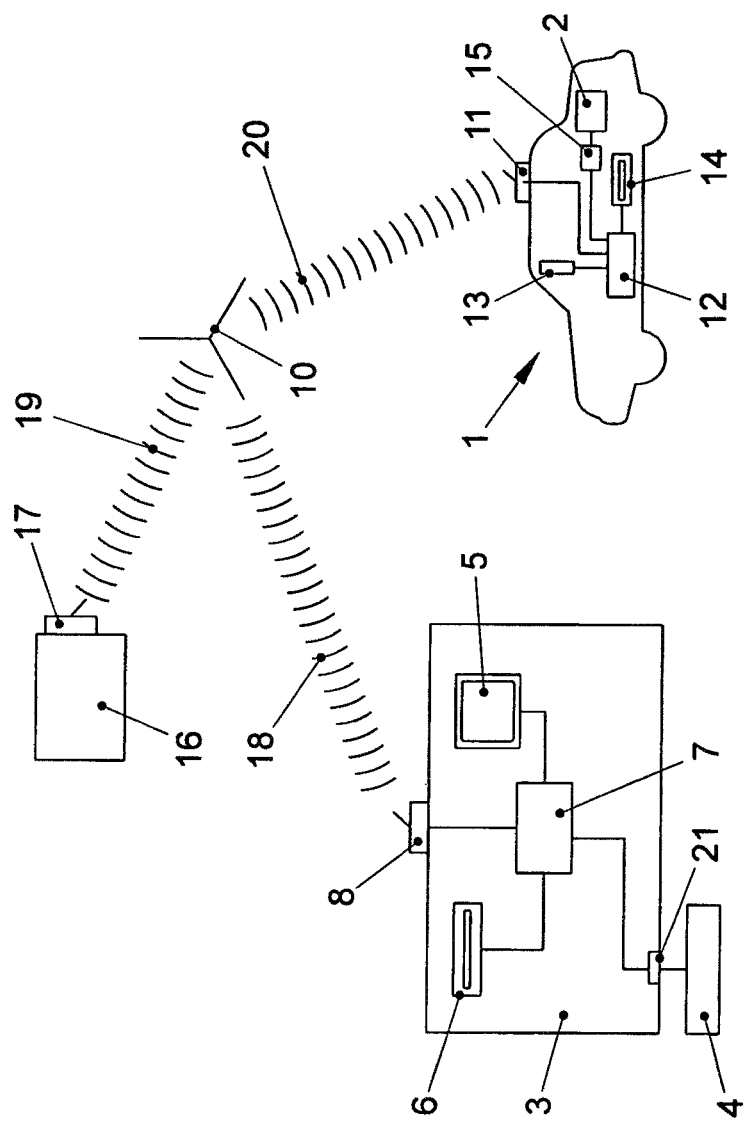
FIG. 1 shows schematically an exemplary embodiment of the device of the invention for carrying out a travel route planning for vehicle.

A basic setup of an exemplary embodiment of the device of the invention is shown schematically in FIG. 1. The device comprises an on-board module and an off-board module, which can exchange data with one another at least at times.

The off-board module may comprise a computer 3, which is connected to an input unit 4 via an interface 21. Input unit 4 can be a keyboard or a mobile device, by which data can be read into computer 3. Computer 3 comprises further a computing unit 7, which is coupled to a data memory 6 and a display device 5, as well as interface 21. A travel route planning for a vehicle 1 can be performed by computer 3, as will be discussed below with reference to an exemplary embodiment of the method of the invention.

The on-board module is situated in a vehicle 1. Vehicle 1 comprises an energy storage device 2. Energy storage device 2 can be made as a rechargeable battery. Said battery provides the energy for powering vehicle 1 and optionally for other internal consumers of vehicle 1. Energy storage device 2, however, can also be a fuel tank, which receives fuel for driving vehicle 1. It is possible in addition that vehicle 1 is a hybrid vehicle, which can be powered both by the energy from a battery and also by means of fuel.

A sensor 15 for determining the remaining amount of energy in energy storage device 2 is provided with energy storage device 2. Said sensor determines the charge state of a rechargeable battery or the level of fuel in a fuel tank.

Furthermore, vehicle 1 comprises an additional computing unit 12, which is coupled in terms of data links to sensor 15, an additional display device 13, and an additional data memory 14.

Computer 3 and vehicle 1 are equipped further with radio interfaces 8 and 11, which are connected to computing unit 7 or computing unit 12. A data transmission 18, 20 between computer 3 and vehicle 1 can be made via a transmission station 11 between interfaces 8 and 11. Therefore, data can be transmitted particularly from computer 3 to computing unit 12 of vehicle 1. The radio connection can be, for example, a mobile radio connection. It would also be possible, however, that it is a wireless network connection (WLAN) or another short-range radio connection, which enables data exchange when vehicle 1 is in the vicinity of computer 3. If the network is a mobile radio connection, it is possible further that computer 3 or computing unit 12 of vehicle 1 exchanges data with an external server 16, which also has a radio interface 17. A data transmission 19, which contains relative information for the route planning, is possible by means of server 16, as will be described later in regard to the exemplary embodiment of the method of the invention.

Figure 2:
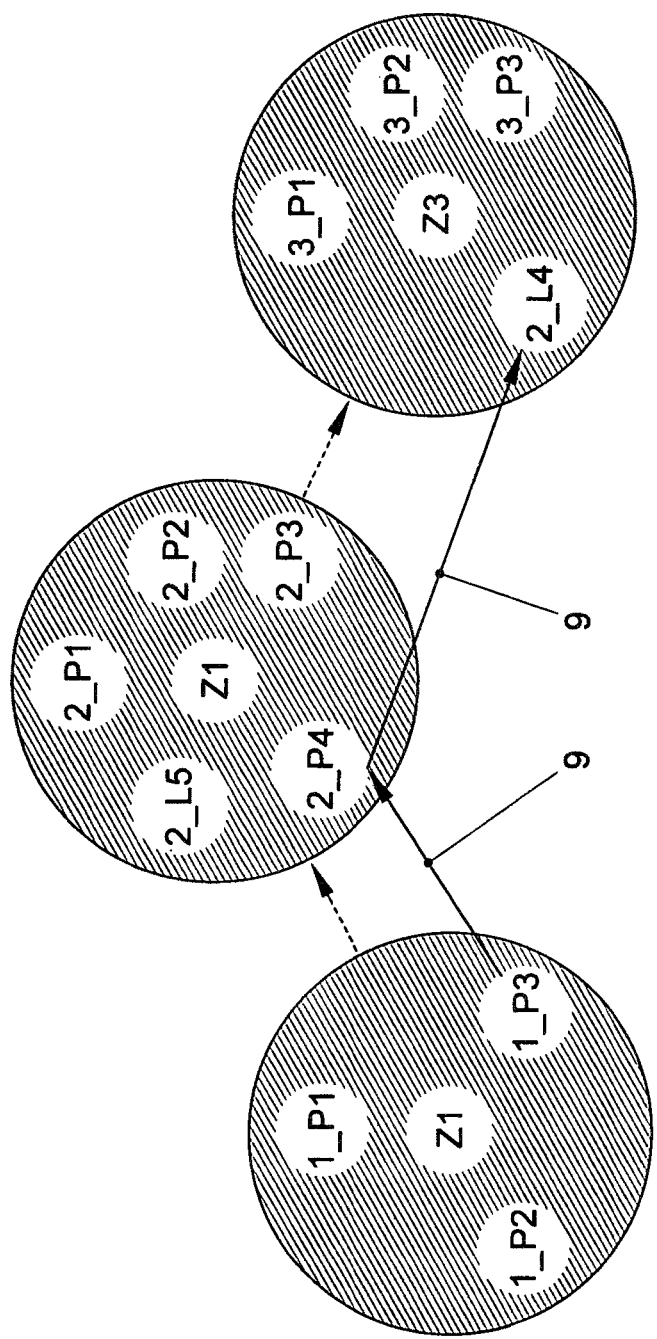
FIG. 2 shows a diagram to illustrate the destinations and the parking areas assigned to the destinations.

An example of a route to be planned is shown schematically in FIG. 2. Via an electronic appointment calendar, a time schedule for a user's day is transmitted via interface 21 to computing unit 7. On this day the user wishes to drive to destinations Z1, Z2, and Z3. These destinations Z1, Z2, and Z3 are assigned different geographic positions. In addition, the schedule data contain time data, which indicate when the user wants to reach destinations Z1, Z2, and Z3 and when he wants to leave them again. The routes to be planned therefore should connect the destination sequence Z1, Z2, and Z3 so that the user can keep the appointments at these destinations Z1, Z2, Z3 at the assigned times. In this regard, it should be assured in addition that the energy reserves in energy storage device 2 of vehicle 1 are sufficient to drive to destinations Z1, Z2, and Z3. In so doing, it is possible that energy storage device 2 is filled at energy supply facilities during the driving of the route sequence.

It is considered furthermore that the user cannot drive directly with his vehicle 1 to destinations Z1, Z2, and Z3 but requires a parking area for a vehicle 1. Data memory 6 therefore contains a list of parking areas whose geographic positions and information on whether the parking area is a parking lot or the parking area comprises an energy supply facility by means of which energy storage device 2 of vehicle 1 can be replenished.

In the case of destinations Z1, Z2, and Z3 shown in FIG. 2, the parking lots 1_P1, 1_P2, 1_P3 are assigned to destination Z1. Parking lots 2_P1, 2_P2, 2_P3, and 2_P4 and energy supply facility 2_L5 are assigned to destination Z2. Parking lots 3_P1, 3_P2, 3_P3 and energy supply facility 3_L4 are assigned to the third destination Z3. Computing unit 7 can determine a route sequence that connects the parking areas assigned to destinations Z1, Z2, and Z3, as is shown by arrow 9.

Figure 3:
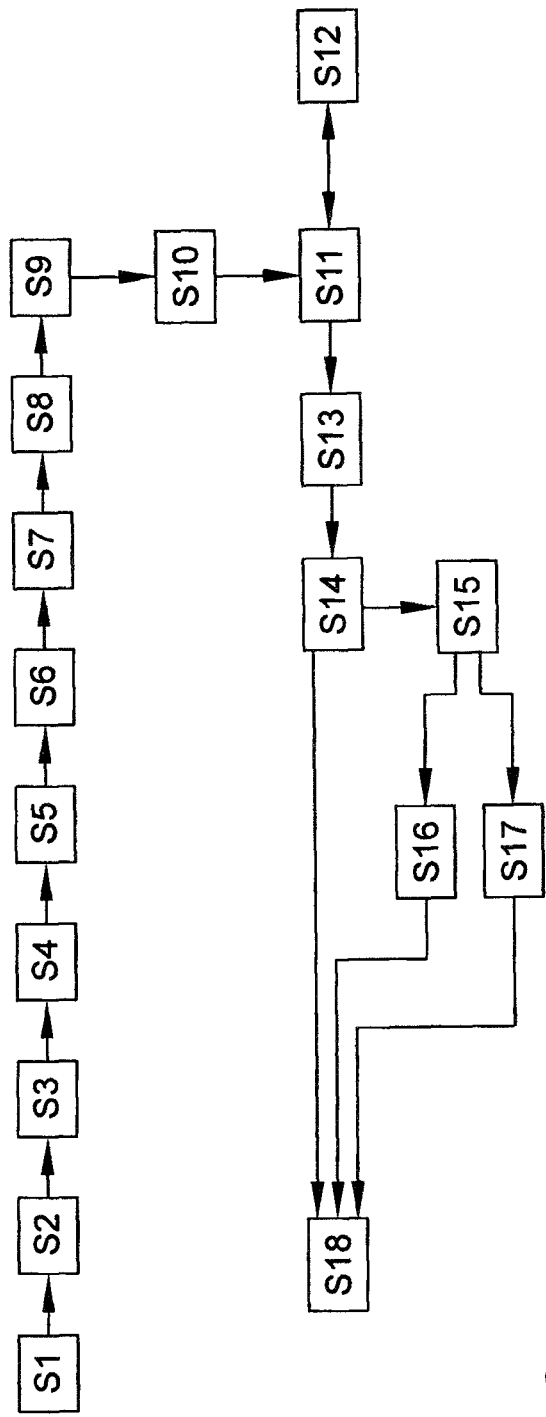
FIG. 3 shows an exemplary embodiment of the method of the invention for carrying out a travel route planning for a vehicle.

An example of a method of this type for carrying out a travel route planning is explained below in regard to FIG. 3:

First, user-specific constraints are transmitted to computing unit 7 of computer 3 via interface 21 in step S1. These constraints can provide the user's preferences. These preferences may concern, for example, the parking areas for the destinations. The user can indicate a maximum distance of a parking area from a destination. Further, he can indicate a specific preference for a parking space type, for example, for a handicap parking space. Furthermore, the user can indicate the priority that will assure that a certain remaining amount of energy is always stored in energy storage device 2 of vehicle 2 during the planned route sequence. Further, the user can indicate how important it is to him that he arrives at the destination on time at the appointment starting times. Optionally, he can indicate a certain tolerance for delays here. For example, the user can indicate that a destination may be reached with a 5-minute delay, if this prevents having to make a stop at an energy supply facility between two destinations, instead of filling energy storage device 2 during an appointment at a parking area at a destination.

Next, in step S2 the user's schedule data are transmitted, for example, from an electronic calendar on a mobile end device of the user by means of interface 21 to computing unit 7. The schedule data contain information on the geographic positions of destinations of the travel route to be planned and associated time data. The time data indicate when an appointment begins at a specific destination and when it ends. Therefore the duration of staying at a specific destination can also be determined from these data.

In step S3, computing unit 7 breaks down the schedule data into a destination sequence with successive destinations. Next, a route sequence with routes is calculated that connects the destinations of the destination sequence. In this regard, computing unit 7 uses a road network, which vehicle 1 can travel on and which is stored in data memory 6. In step S4, different routes are determined for this, which connect successive destinations of the destination sequence. For each route, in step S5 then the traffic for traveling the route is estimated. For this purpose, computing unit 7 can use historical traffic data stored in data memory 6. In addition, traffic data can be transmitted to computing unit 7 from external server 16 via radio connections 19 and 18. Further, traffic data can also be considered which were generated from another vehicle currently participating in traffic (so-called XFCD—extended floating car data). Furthermore, traffic data can be considered that were transmitted by a vehicle-to-vehicle or vehicle-to-X communication. This allows computing unit 7 to estimate the traffic volume for traveling a route.

Furthermore, computing unit 7 in step S6 can estimate the speed of vehicle 1 in traveling a route. In this estimation, the computing unit can consider the type of traveled streets, which is stored together with the road network in data memory 6. Further, computing unit 7 can consider user-specific data on the driving behavior of the driver for driving along the route sequence. Such driver-specific data can also be stored in data memory 6. They can be obtained, for example, from past trips of this driver.

In step S7, a rough estimation can be performed from the lengths of the different routes, connecting the destinations, the estimation of the traffic in traveling the route, and the driver-specific data on how much time the driver will need to travel the individual routes. Then, alternative route sequences are determined which require as little time as possible to reach the destinations.

Now, in step S8 the remaining amount of energy in energy storage device 2 for traveling the route sequence is predicted by computing unit 7. In this regard, the energy consumption of vehicle 1 and the features of the road network in traveling the route sequences are considered. For example, the gradient of a street of the road network can be considered, as the gradient affects the energy consumption of vehicle 1. Further, delays or accelerations because of curves can be taken into account, because these also affect the energy consumption of vehicle 1. Furthermore, the predicted remaining amount of energy in the energy storage device is taken into account in an iterative method. The charge state of a rechargeable battery or the amount of fuel in the tank of vehicle 1 influences the vehicle's energy consumption. If the battery charge state is rather low, a greater change in the charge state when traveling a route results than when the battery charge state is higher. Further, internal consumers of vehicle 1 are taken into account in the predicted energy consumption. For example, it is possible to determine the probability whether the air-conditioning unit will be turned on when traveling the route. Further, user behavior of the driver of vehicle 1 can be considered. The data from which the energy consumption and thereby the remaining amount of energy in energy storage device 2 for traveling the route sequence are predicted, are stored in data memory 6. They can be read by computing unit 7 and accordingly considered in the prediction.

In step S9, computing unit 7 selects preferred route sequences. In this regard it is especially considered whether the particular remaining amount of energy in the geographic positions of the route sequence is sufficient to reach the destinations of the destination sequence. If not all destinations can be reached with the starting amount of energy in energy storage device 2 of vehicle 1, it is necessary that energy storage device 2 is filled when traveling the route sequence. The geographic positions of energy supply facilities are stored for this purpose in data memory 6. Computing unit 7 preferably selects such a route sequence in which energy storage device 2 of vehicle 1 can be filled, while vehicle 1 is at a parking area assigned to a destination of the destination sequence during a user's appointment.

For selecting the parking area a destination area is established in step S10 for the destinations of the destination sequence. The size of the destination area depends on the maximum distance that a parking area may have from the destination. This maximum distance can have been input by the user in step S1. The geographic positions of all parking areas of the road network are stored in data memory 6. The parking areas located within the destination area and associated with a specific destination, can now be determined. Furthermore, stored in data memory 6 is the information whether the parking area is a parking lot or whether the parking area comprises an energy supply facility (see FIG. 2).

In step S11, an assigned parking area is determined for each destination of the destination sequence. The following factors are considered here:

The prediction for the remaining amount of energy in energy storage device 2 of vehicle 1 determines whether it is necessary for the parking area to include an energy supply facility. If so, only parking areas with energy supply facilities are considered in the subsequent selection. If not, only parking lots are considered.

Furthermore, the distance of the parking area from the assigned destination is considered, and possibly the length of time needed by the user to reach the destination from the parking area. In this regard it can also be considered whether the user goes by foot from the parking area to the destination or reaches the destination from the parking area in some other way. A length of time the user needs for going from the parking area to the assigned destination can be determined from the distance and how the destination is reached from the parking area. In this regard, user-dependent walking speeds can also be considered which are stored in data memory 6.

Furthermore, the geographic position of the next destination or the geographic position of the parking areas of the next destination or a selected parking area of the next destination is considered. Alternatively or in addition, the geographic position of the prior destination or the geographic position of the parking areas of the prior destination or a selected parking area of the prior destination is considered. This consideration may mean that the parking area next to a destination is not always the most advantageous. If the route to reach the destination and the next destination is prolonged by this parking area, another parking area can be more favorable from the standpoint of time although it is farther from the assigned destination.

The parking areas assigned to the destinations are now selected by computing unit 7 so that neither time nor energy conflicts arise. This means that the energy reserves in the energy storage device of vehicle 1 in traveling the route sequence are sufficient to reach the parking areas assigned to the destinations, whereby it is considered that energy storage device 2 can be replenished partially or completely at parking areas with energy supply facilities. It is assured further that the user will reach the destinations on time, i.e., in accordance with the schedule data, whereby not only the time needed to travel the routes between parking areas is taken into account but also the length of time a user needs to reach the assigned destination from the parking area.

In step S12, the availability probability of the parking areas within the destination area to the destinations can be determined as well. To this end, in a step S11, the arrival time of the vehicle at the parking area to be analyzed and the length of stay at this parking area can be determined and compared with historical data stored in data memory 6. Furthermore, already made reservations by third parties for the parking areas can be retrieved from external server 16 via data links 18 and 19. If reservations for a desired time have already been made, the availability probability of the respective parking area is very low or zero. Such parking areas are then not considered in step S11 by computing unit 7 for the route sequence.

Next, in step S13 a detailed planning of the route sequence is carried out. In so doing, the routes between two parking areas associated with successive destinations of the destination sequence are again optimized in terms of time and energy.

Then, in step S14, an optimization of the routes in the daily routine is made, whereby it is assured in particular that the route sequence matches the desired schedule data in terms of time. It is assured that the user arrives at the appointment starting times at the appropriate geographic positions. In this regard, the usable time of the user is also optimized. This means in particular that the amount of energy in energy storage device 2 of vehicle 1 is increased when vehicle 1 is not in use during a user's appointment. When computing unit 7 was able to calculate a route sequence without any time or energy conflicts with the schedule data, the calculated route sequence can be displayed in step S18 by a display device 5 or output via a radio interface 8. The details of the visualization of the route sequence will be explained below.

Should it turn out, however, that a route sequence not conflicting with the schedule data in terms of time is not calculable by computing unit 7, various alternative route sequences are tested by computing unit 7 in step S15. In so doing, first the energy and geographic constraints remain unchanged; i.e., the destination sequence corresponding to the schedule data should continue to be covered by the route sequence. Further, computing unit 7 assures that the predicted amount of energy in energy storage device 2 of vehicle 1 is sufficient to reach all destinations of the destination sequence, whereby it is considered that in traveling the route sequence energy storage device 2 can be filled in the interim by the energy supply facilities. A route sequence is therefore calculated that comes as close as possible to the desired schedule data in terms of time.

In step S16, then adjusted schedule data are then output with an assigned route sequence that generates no conflicts with the adjusted schedule data. The user can accept the adjusted schedule data by means of input unit 4. They are then transmitted to the electronic calendar via interface 21. If necessary, messages for other participants in the appointments are automatically generated to inform them of the adjusted schedule data.

If it is not possible to calculate a route sequence based on adjusted schedule data, without any time or energy conflicts a route sequence is calculated in step S17, in which a destination or a number of destinations were deleted. These changes in schedule data and the adjusted route sequence are output. If the user accepts the adjusted route sequence and the changed schedule data, the adjusted route sequence is stored as the current route sequence and the changed schedule data are transmitted to the user's electronic calendar.

As soon as the route sequence for the travel route planning is definite, the calculated route sequence is displayed in step S18 and output. Furthermore, computing unit 7 reserves the desired parking areas of the route sequence via data links 18 and 19 in external server 16.

According to a refinement of the exemplary embodiment of the method of the invention, various uncertainties still arising in the travel route planning are determined and linked together. On the one hand, an uncertainty can be determined that the driver reaches the predicted arrival time at a parking place at a particular time. Also, the probability can be considered that the driver in fact also leaves the parking area at the predicted departure time. The probabilities can be depicted by curves showing different heights, i.e., probabilities, and have different widths, i.e., different deviations from the predicted value.

Furthermore, a deviation probability from the nominal traffic flow can be considered. In combination with the uncertainty that the driver reaches or again leaves a specific parking area at the predicted time, probabilities for traffic-related arrival and departure times can be calculated.

Further, an uncertainty can be considered related to the occupation of an energy supply facility or a parking lot. If necessary, vehicle 1 must wait for a certain time until the parking area or energy supply facility becomes free. As a result, the probabilities for the arrival and departure times can be further modified.

The combinations of the probability distribution can be used by computing units 7 and 12 for optimizing the advance planning of the route sequence or for optimizing the route sequence during the trip. This will maximize the predictability and planability of the travel route in the network.

Figure 4:
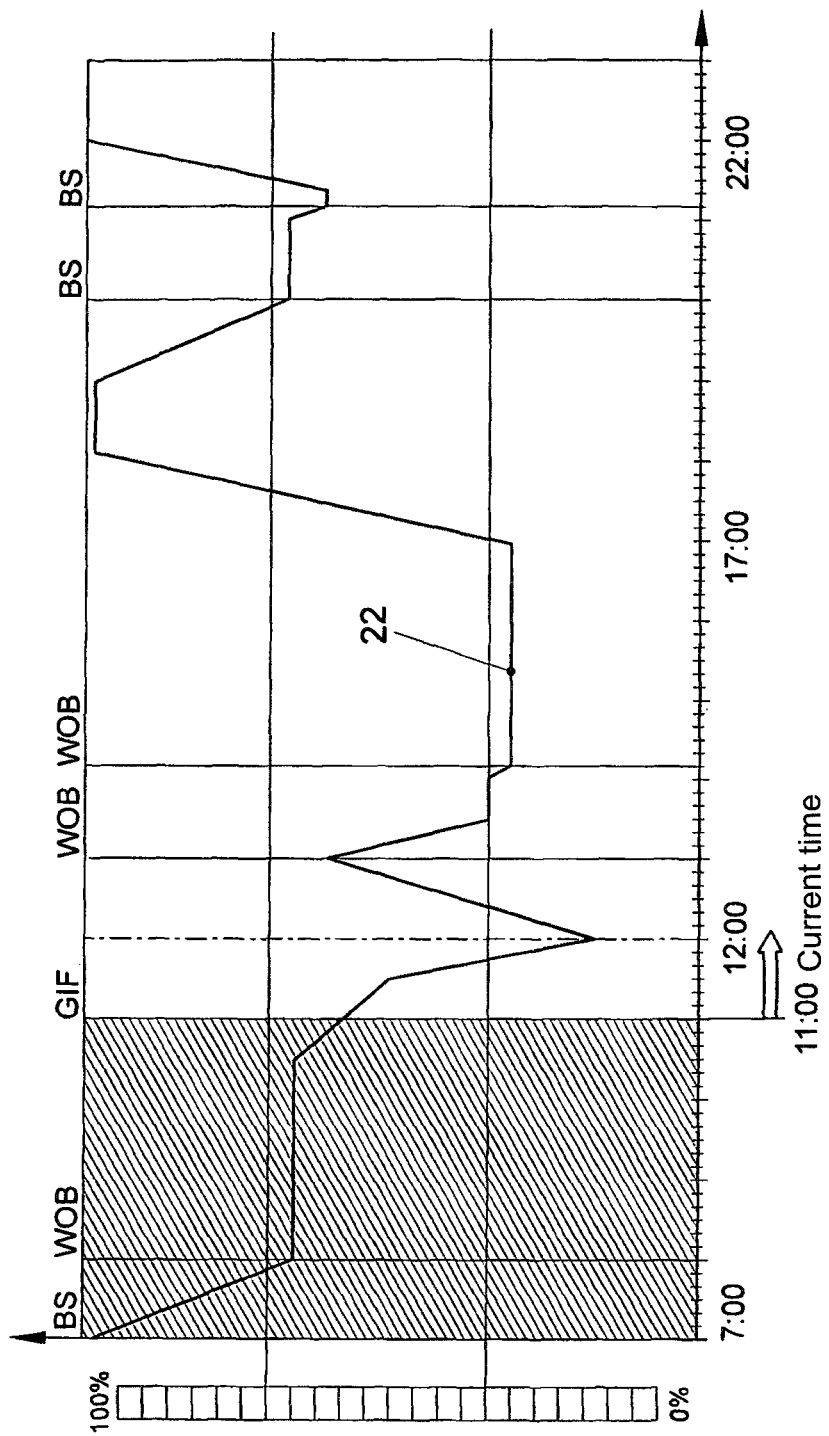
FIG. 4 shows a graphic illustration with a curve, which shows the remaining amount of energy when traveling the route sequence.

How the output of the travel route planning calculated by the above-described method occurs will be described below with reference to FIGS. 4 to 12:

In FIG. 4 the predicted remaining amount of energy for the route sequence is shown as it can be displayed to the user. A coordinate system is shown on whose horizontal axis time is plotted and on whose vertical axis the remaining amount of energy in energy storage device 2 of the vehicle is plotted from 0% to 100%. The abbreviations for locations that are reached at the particular times in the route sequence are also shown on the horizontal axis. It is evident from the shown curve 22, for example, that at 7:00 o'clock the vehicle drives from Braunschweig towards Wolfsburg. There is idle time for the vehicle in Wolfsburg. At 12:00 o'clock, energy storage device 2 of vehicle 1 is filled. Energy storage device 2 is again filled at 17:00 o'clock and shortly before 22:00 o'clock. It is evident in addition from curve 22 that if energy storage device 2 would not have been filled at 12:00 o'clock, the energy reserves would have been used up while traveling the route of the route sequence. This would have led to an energy conflict with the result that the driver would have been stranded with the vehicle.

Figure 5:
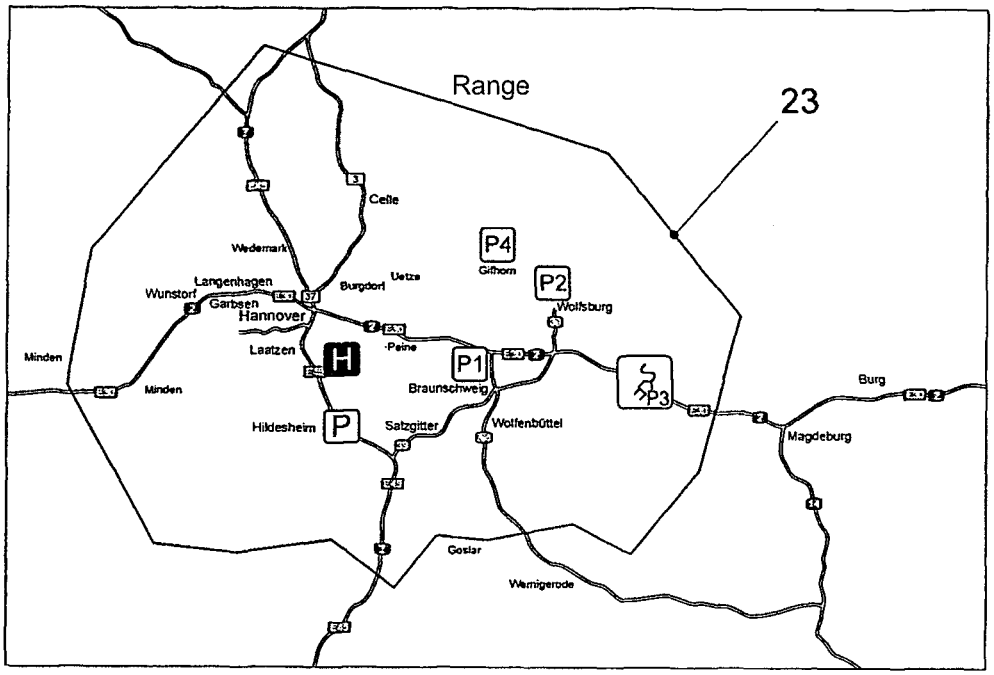
FIGS. 5 to 12 show graphic map displays with additional information on the route sequence.

Furthermore, as shown in FIG. 5, after the calculation of the route sequence with use of the road network stored in data memory 6, a graphic map display can be generated, in which the geographic positions of the parking areas associated with the destinations can be depicted by means of symbols P1 to P4. If a parking area has an energy supply facility, a symbol is shown in addition which indicates that, for example, the battery of the electric vehicle can be charged. Furthermore, the geographic position of a reference position H is indicated. The reference position can be, for example, the user's place of residence or his workplace.

If one assumes that the user starts the route sequence at reference position H, based on the starting amount of energy in energy storage device 2 of the vehicle and based on the stored road network it is determined which points of the road network can still be reached from reference position H. In this range, the predicted energy consumption in traveling the road network is considered as well. In the graphic map display, a boundary line 23 is now shown which visualizes the range of vehicle 2 at geographic reference position H. Boundary line 23 delimits the area with the points of the road network reachable from the position of vehicle 2 with the remaining amount of energy of energy storage device 2.

Figure 6:
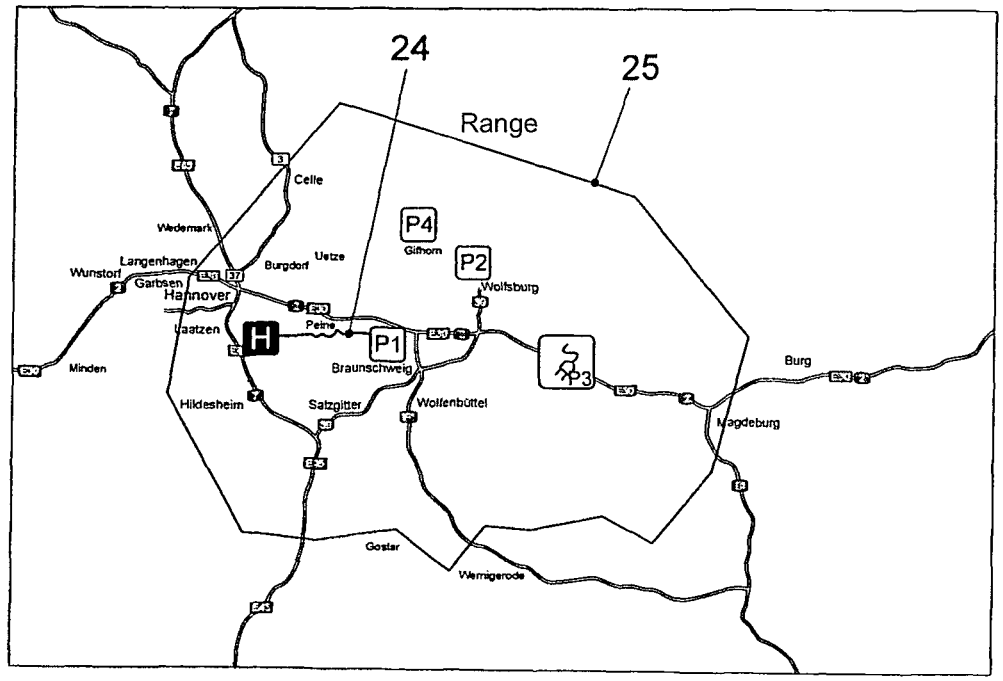

In another illustration reproduced in FIG. 6, on the one hand, route 24 assigned to the first destination from geographic reference position H to parking area P1 is shown. Further, the remaining amount of energy in energy storage device 2 of vehicle 1 at the geographic position of parking area P1 is predicted as described above. For said remaining amount of energy, the range of vehicle 1 is again determined: i.e., points of the road network are determined that are still reachable from parking area P1 with the predicted remaining amount of energy. For this range area, a boundary line 25 is again indicated on the graphic map display.

Figure 7:
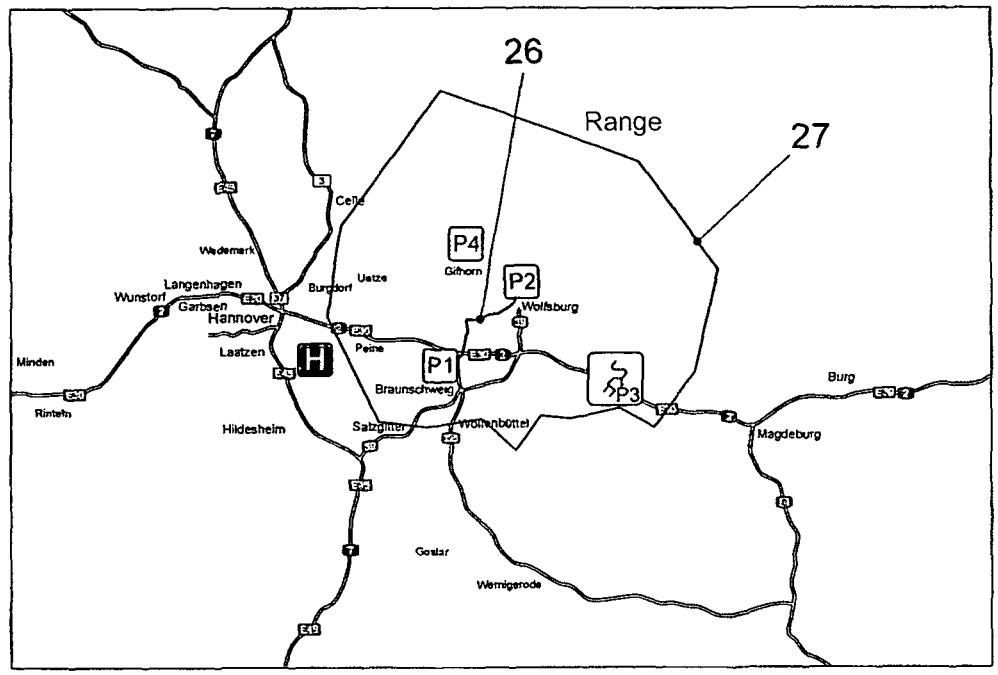

In FIG. 7, route 26 from parking area P1 of the first destination to parking area P2 of the second destination is shown on the graphic map display. Furthermore, as in the visualization according to FIG. 6, the range of vehicle 2 with the predicted remaining amount of energy in parking area P2 is determined and shown based on boundary line 27.

Figure 8:
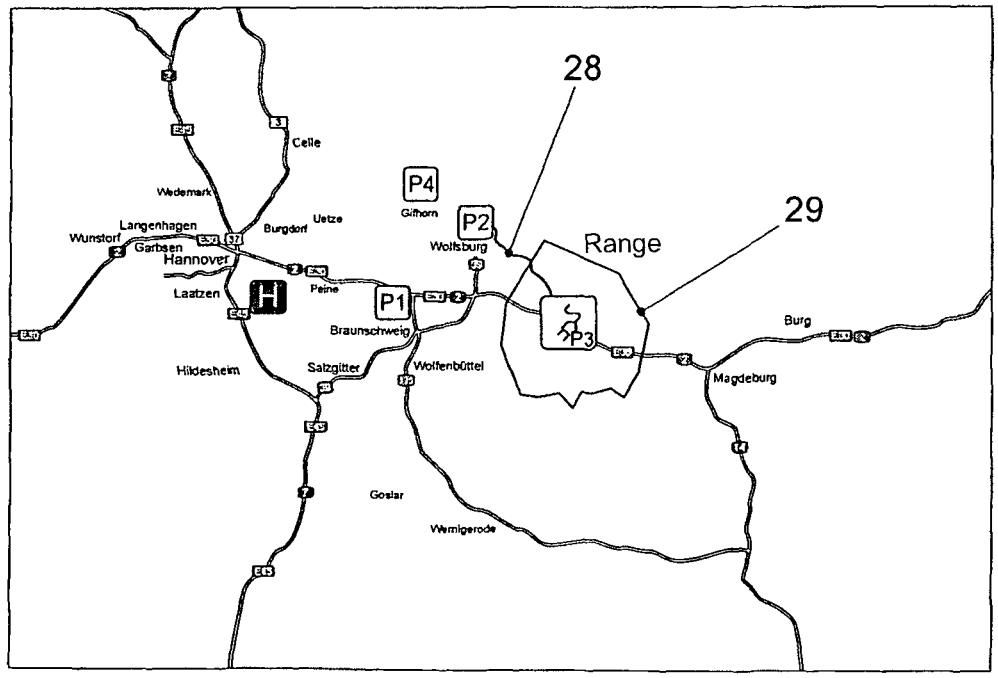
Figure 9:
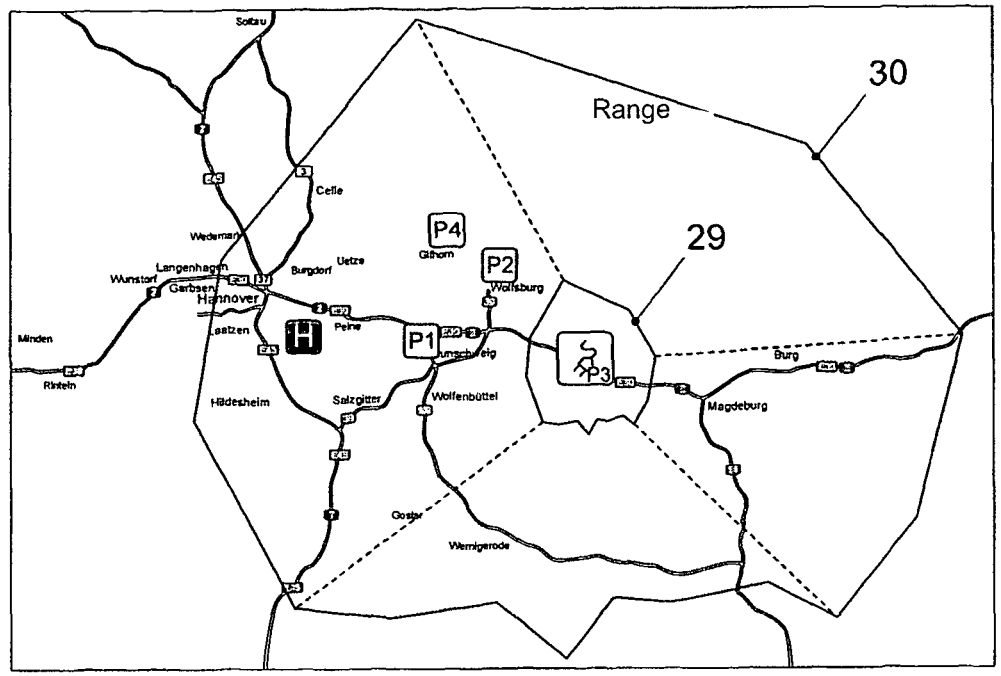

Likewise, in the illustration according to FIG. 8, route 28 from parking area P2 of the second destination to parking area P3 of the third destination is indicated on the graphic map display. Further, a boundary line 29 for the remaining range at parking area P3 is shown. As is evident from FIG. 8, this remaining range is no longer sufficient for vehicle 2 to reach parking area P4 of the fourth destination. The route sequence, however, was calculated in advance so that a parking area which comprises an energy supply facility was selected at the third destination. Energy storage device 2 of vehicle 1 thus can be filled at parking area P3. As shown in FIG. 9, the remaining range of vehicle 1 at parking area P3 is shown with boundary line 29 before the filling of energy storage device 2 and with boundary line 30 after the filling of the energy storage device. As is evident from FIG. 9, the remaining range after filling of energy storage device 2 is sufficient to reach parking area P4 for the next destination. In addition, the remaining range is sufficient to reach reference position H.

Figure 10:
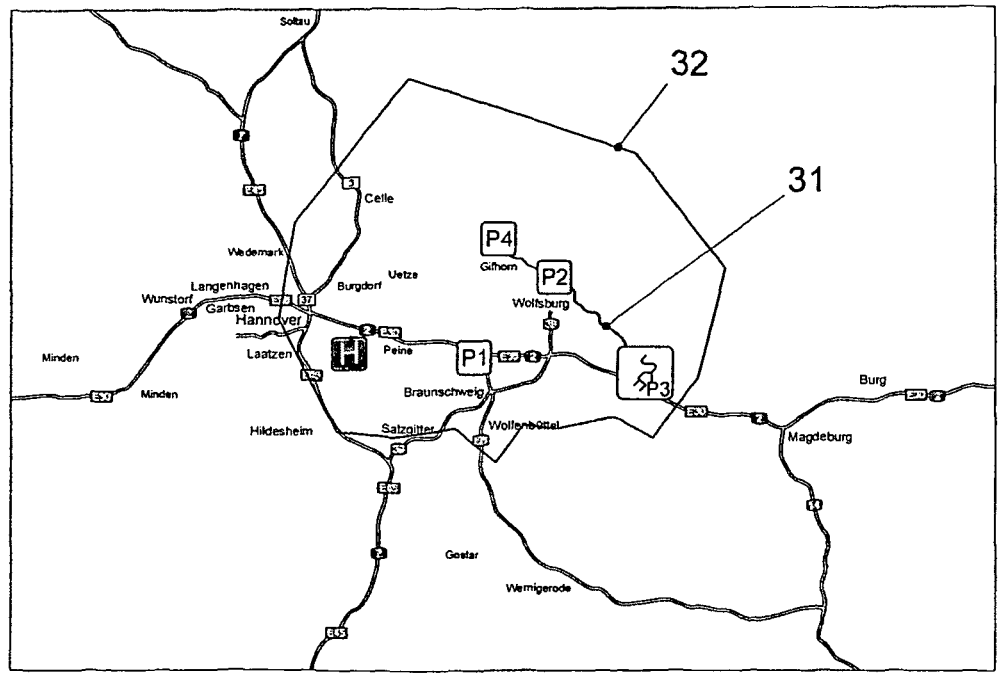

In FIG. 10, finally route 31 from parking area P3 to parking area P4 of the fourth destination is shown on the graphic map display. Further, the remaining range of vehicle 1 at parking area P4 is shown with boundary line 32. It is evident in particular that reference position H continues to be within the remaining range. Therefore, it is assured in the route sequence that reference position H can always be reached.

Figure 11:
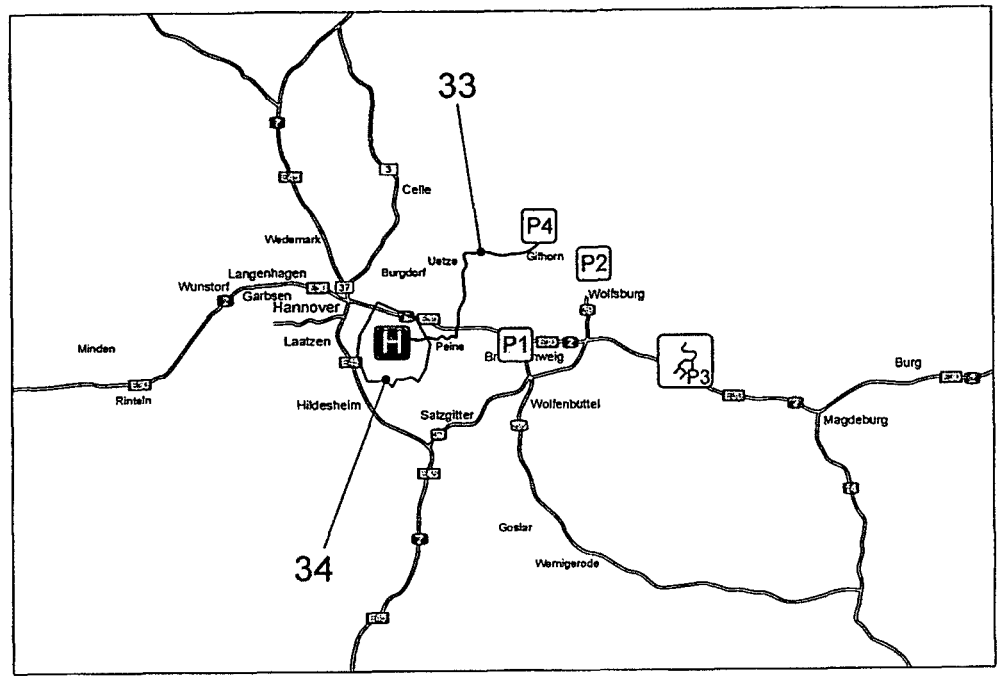

In FIG. 11, finally route 33 is shown on the graphic map display, which leads from parking area P4 back to reference position H. The remaining range at reference position H at the end of the route sequence is shown with boundary line 34. This leaves a relatively low remaining amount of energy at the end of the route sequence. Energy storage device 2 of the vehicle therefore should be replenished at reference position H.

Figure 12:
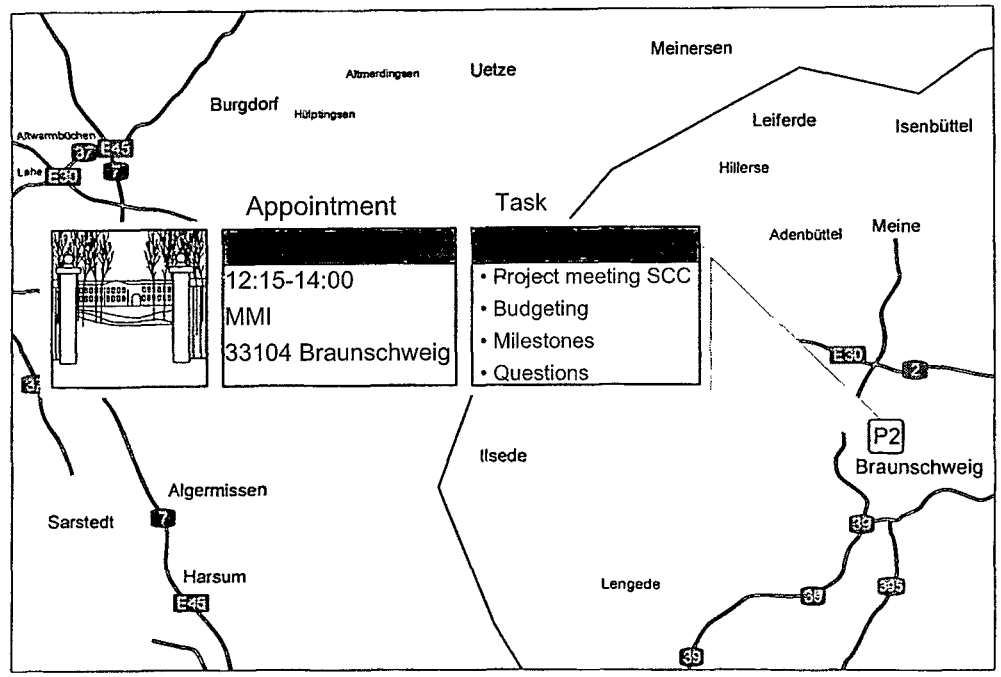

Additional information on a parking area P2 is shown in FIG. 12. Said additional information can also be called up by the user by operating input unit 4 before the start of the trip or, as will be described below, also during the trip.

An example for the method for performing travel route planning for a vehicle was described with reference to FIG. 3. After the travel route planning has been completed and a route sequence is available, it is used during traveling the route sequence to offer route guidance to the user in the vehicle and to adjust the route sequence if necessary. An example for these additional process steps will be described below:

First, data on the route sequence determined by computing unit 7 are transmitted to computing unit 12 in vehicle 1 via data links 18 and 20. Computing unit 12 is substantially configured like computing unit 7. Further, data memory 14 in vehicle 1 has the same information as data memory 6 of computer 3. If necessary, data memories 6 and 14 can also be synchronized via data links 18, 20.

During the trip, navigation information for traveling the route sequence is now output via display device 13 to the driver of vehicle 1. Computing unit 12 therefore provides a conventional vehicle navigation system in conjunction with display device 13. For this purpose, computing unit 12 is also coupled to a receiver for satellite signals, for example, a GPS receiver. Said receiver can also be integrated into computing unit 12.

At the same time, computing unit 12 continuously transmits data of sensor 15 on the remaining amount of energy in energy storage device 2. If the deviation of the determined remaining amount of energy in energy storage device 2 of vehicle 1 from the predicted remaining amount of energy during the calculation by computing unit 7 exceeds a specific limit value, e.g., 10% of the predicted remaining amount of energy, the route sequence can be recalculated based on the determined remaining amount of energy. If the first remaining amount of energy is less than the predicted remaining amount of energy, it is checked in particular whether the remaining amount of energy is sufficient to still reach all destinations and energy supply facilities. This not being the case, the route sequence is recalculated by computing unit 12 and output, as was explained in regard to FIG. 3.

Furthermore, the current position is compared with the predicted position at a specific time. If there is a time deviation, particularly if a geographic position of the route sequence has still not been reached at a specific time, it is checked whether the destinations of the route sequence can continue to be reached at the associated time data of the schedule data. In this regard, the predicted remaining amount of energy in the energy storage device of the vehicle for upcoming sections of the route sequence is also taken into account. If, for example, it is necessary because of the actual energy consumption to insert an unplanned intermediate stop or number of unplanned intermediate stops for replenishing the amount of energy in energy storage device 2, the additional time necessary for said intermediate stop is taken into account.

Furthermore, current traffic data can be considered which are transmitted to computing unit 12 via data links 19 and 20 from an external server 16. Depending on the current traffic data, an updated time for reaching the next destination can be calculated. Further, the route sequence can be updated in terms of time. It is checked in this case as well whether the destinations of the route sequence can still be reached at the associated time data of the schedule data.

Should it turn out that certain appointments cannot be kept in terms of time, an output for the driver is generated so that he can adjust the appointments accordingly and can inform other participants in the appointments.

Computing unit 12 in this case calculates an adjusted route sequence, in which the time data of the schedule data were adjusted or certain appointments were deleted, as has already been explained above.

Furthermore, the probabilities for the availability of parking areas of the route sequence can be updated. Corresponding data can be transmitted to computing units 12, for example, via data links 19, 20 from external server 16. Should it turn out, for example, that a specific parking lot is no longer free, computer unit 12 adjusts the route sequence so that another parking lot is selected for a specific destination in the route sequence. If it turns out that a parking area with an energy supply facility is not free at the desired time of the route sequence, computing unit 12 can select a different parking area with an energy supply facility for an adjusted route sequence. Said other parking area with the energy supply facility may be located at a different destination. During the optimization of the route sequence, computing unit 12 maximizes the time available for the user. Possible waiting times for the refilling of the energy storage device 2 are minimized thereby and possibly arranged at times when the user is at his appointment.

In all adjustments of the route sequence during the trip, adjusted graphic map displays and diagrams are also generated, as shown in FIGS. 4 to 12, and output on request via a display device 13 in vehicle 1.

A comprehensive calculation of a driving task with a destination sequence and corresponding location, time, and energy restrictions can be calculated by the travel route planning of the invention. In this regard, particularly during planning for replenishing of energy reserves of vehicle 1, a linked overview of all destinations of the destination sequence is made. This is important particularly when vehicle 1 is an electric vehicle with a limited range. Further, not only the trip routes for vehicle 1 are considered but also the paths from the parking areas of vehicle 1 to the desired destinations. The length of time for these paths are included in the calculation of the route sequence and particularly in the selection of the parking areas for the destinations.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A method for carrying out travel route planning for a vehicle, the method comprising:

transmitting schedule data, which comprise geographic positions of destinations of the travel route to be planned and associated time data, to a computing unit that is coupled to a data memory, in which data based on a road network for the vehicle and data based on geographic positions of energy supply facilities are stored;

checking, via the computing unit, whether a route sequence that connects the geographic positions of the destinations associated with the schedule data is calculable, so that destinations are reached at the associated time data of the schedule data, wherein a predicted remaining amount of energy in an energy storage device of the vehicle for traveling the route sequence is determined and taken into account;

storing further data on geographic positions of parking areas comprising parking lots or energy supply facilities for the vehicle for the destinations of the route sequence in the data memory;

determining, via the computing unit in calculating a route sequence also for the destinations of a destination sequence case, parking areas assigned to the destinations at the particular destination, determining an assigned parking area for each destination of the destination sequence, wherein, in determining the distance of the parking area from an assigned destination, the geographic position of the next destination or the geographic position of the parking areas of the next destination and the predicted remaining amount of energy in the energy storage device for traveling the route sequence are taken into account, and wherein the route sequence comprises routes between parking areas of successive destinations of the destination sequence;

checking whether a route sequence connects the geographic positions of the destinations associated with the schedule data so that the destinations are reached at the associated time data of the schedule data, wherein a length of time is taken into account that the user requires to reach the destination from the parking area assigned to the destination;

determining, if no such route sequence is calculable by the computing unit, adjusted schedule data for which such a route sequence is calculable; and outputting the adjusted schedule data, wherein, during said checking, a probability of parking area availability at said destinations is taken into consideration, wherein the energy supply facilities are located in the parking area at said destinations, wherein, during said checking, time data for the destinations and a length of time for increasing energy reserves while the vehicle is at the destination is taken into consideration, wherein said increasing energy reserves includes a possibility of ending charging of the energy storage device before the energy storage device is filled so that destinations are reached at the associated time data of the schedule data, and wherein, during said checking, driving behavior based on historical data for a specific driver is taken into consideration, the driving behavior including historical driving speed data.

2. The method according to claim 1, wherein, in the adjusted schedule data new time data are assigned to geographic positions of destinations.

3. The method according to claim 1, wherein destinations are deleted in the adjusted schedule data.

4. The method according to claim 1, wherein, in calculating the route sequence, the computing unit optimizes a time usable for a user of the vehicle.

5. The method according to claim 1, wherein the computing unit calculates the predicted remaining amount of energy in the energy storage device based on a predicted energy consumption for traveling the route sequence, and wherein the predicted energy consumption for driving the vehicle and a predicted energy consumption of internal consumers of the vehicle are taken into account.

6. The method according to claim 5, wherein in determining the predicted energy consumption of internal consumers of the vehicle, weather forecasts and/or season in which the route sequence is to be traveled is taken into account.

7. The method according to claim 1, wherein, during traveling of the calculated route sequence, the remaining amount of energy in the energy storage device of the vehicle is determined and compared with the predicted remaining amount of energy of the vehicle for a respective route position and, if a deviation of the determined amount of energy from the predicted remaining amount of energy exceeds a limit value, it is checked whether the destinations of the route sequence can continue to be reached at the associated time data of the schedule data, and wherein the predicted remaining amount of energy in the energy storage device of the vehicle for traveling the route sequence is determined.

8. The method according to claim 7, wherein, if the check shows that the destinations of the routes cannot be reached at the associated time data, an adjusted route sequence is calculated or adjusted schedule data are determined and the adjusted route sequence or the adjusted schedule data are output.

9. The method according to claim 1, wherein the energy storage device stores energy for driving the vehicle.

10. The method according to claim 1, wherein the route sequence comprises a series of routes that connects the destinations.

11. The method according to claim 1, wherein the associated time data includes a starting time for an appointment and an ending time for an appointment.

12. The method according to claim 1, wherein said probability of parking area availability at said destinations is determined based on historical data indicating statistically the times at which individual parking areas where occupied.

13. The method according to claim 1, wherein said historical data comprises driver profiles based on driving behavior of the specific driver.

14. The method according to claim 1, further comprising displaying a visualization of a remaining range for a route sequence and marking, with respect to the destinations, an area reachable from a current destination with a remaining amount of energy in the storage device.

15. A device for travel route planning for a vehicle, the device comprising:
an energy storage device for storing energy for driving the vehicle;
a computing unit;
a data memory that is coupled to the computing unit and in which data based on a road network and data based on geographic positions of energy supply facilities for the vehicle are stored;
an interface that is coupled to the computing unit and via which schedule data, which comprises geographic positions of destinations of the travel route to be planned and associated time data, are adapted to be transmitted to the computing unit;
an output unit coupled to the computing unit and via which a route sequence calculated by the computing unit and/or adjusted schedule data is configured to be output;
wherein, via the computing unit, it is checked whether a route sequence is calculable that connects the geographic positions of the destinations associated with the schedule data so that the destinations are reached at an associated time data of the schedule data,
wherein a predicted remaining amount of energy in the energy storage device of the vehicle for traveling the route sequence is determined and taken into account, and if no such route sequence is calculable, adjusted schedule data for which such a route sequence is calculable is determined by the computing unit,
wherein, during said checking, a probability of parking area availability at said destinations is taken into consideration,
wherein the energy supply facilities are located in the parking area at said destinations,
wherein, during said checking, time data for the destinations and a length of time for increasing energy reserves while the vehicle is at the destination is taken into consideration,
wherein said increasing energy reserves includes a possibility of ending charging of the energy storage device before the energy storage device is filled so that destinations are reached at the associated time data of the schedule data,
wherein, during said checking, driving behavior based on historical data for a specific driver is taken into consideration, the driving behavior including historical driving speed data,
wherein the device has an off-board module and an on-board module,
wherein the off-board module comprises the computing unit, wherein the off-board and on-board modules are coupled to one another via an interface at least at times in terms of data links, so that at least one route sequence is transmitted from the off-board module to the on-board module,
wherein the on-board module comprises an additional computing unit, an additional output unit, a memory for storing the route sequence transmitted from the off-board module, and a sensor for determining the remaining amount of energy in the energy storage device of the vehicle,
wherein during the traveling of the calculated route sequence, the determined remaining amount of energy in the energy storage device of the vehicle is compared via the additional computing unit with the predicted remaining amount of energy of the vehicle for a corresponding route position of the route sequence stored in the memory and, if the deviation of the detected remaining amount of energy from the predicted remaining amount of energy exceeds a limit value, it can be checked via an additional computer unit whether the destinations of the route sequence can be reached at the associated time data of the schedule data, where in the predicted remaining amount of energy in the energy storage device of the vehicle for traveling the route sequence is determined, and wherein, if a check shows that the destinations of the route sequence cannot be reached at the associated time data, the additional computing unit calculates an adjusted route sequence for outputting via the additional output unit or determines adjusted schedule data.

* * * * *